(12) United States Patent
Sohn et al.

(10) Patent No.: US 9,038,469 B2
(45) Date of Patent: May 26, 2015

(54) REFERENCE FREE INCONSISTENCY DETECTION SYSTEM

(75) Inventors: Hoon Sohn, Seoul (KR); Hyung Jin Lim, Andong (KR); Chul Min Yeum, Cheongju (KR); Jeong-Beom Ihn, Bellevue, WA (US)

(73) Assignee: THE BOEING COMPANY, Chicago, IL (US)

( * ) Notice: Subject to any disclaimer, the term of this patent is extended or adjusted under 35 U.S.C. 154(b) by 803 days.

(21) Appl. No.: 13/312,341

(22) Filed: Dec. 6, 2011

(65) Prior Publication Data
US 2013/0139598 A1 Jun. 6, 2013

(51) Int. Cl.
*G01N 29/06* (2006.01)
*G01N 29/07* (2006.01)
*G01N 29/04* (2006.01)
*G01N 29/44* (2006.01)

(52) U.S. Cl.
CPC .......... *G01N 29/043* (2013.01); *G01N 29/4454* (2013.01); *G01N 2291/0231* (2013.01); *G01N 2291/044* (2013.01); *G01N 2291/2694* (2013.01); *G01N 29/07* (2013.01)

(58) Field of Classification Search
CPC . G01N 29/014; G01N 29/043; G01N 29/048; G01N 29/069; G01N 29/07; G01N 29/075
USPC ............................................. 73/597, 598, 602
See application file for complete search history.

(56) References Cited

U.S. PATENT DOCUMENTS

| | | | |
|---|---|---|---|
| 4,658,649 A | 4/1987 | Brook | |
| 7,024,315 B2 | 4/2006 | Giurgiutiu | |
| 7,720,626 B2 | 5/2010 | Mathews | |
| 7,822,573 B2 | 10/2010 | Ihn | |
| 8,042,397 B2 * | 10/2011 | Ihn | 73/603 |
| 8,286,492 B2 | 10/2012 | Sohn et al. | |
| 8,499,632 B1 * | 8/2013 | Ihn et al. | 73/587 |
| 8,707,787 B1 | 4/2014 | Sohn et al. | |
| 2003/0009300 A1 * | 1/2003 | Giurgiutiu | 702/35 |
| 2008/0283332 A1 | 11/2008 | Ihn | |
| 2009/0192729 A1 * | 7/2009 | Pado et al. | 702/36 |
| 2012/0255359 A1 | 10/2012 | Sohn et al. | |

OTHER PUBLICATIONS

Sohn et al., "Time Delay Based Health Monitoring System Using a Sensor Network," U.S. Appl. No. 13/084,276, filed Apr. 11, 2011, 71 pages.
Hall et al., "Minimum variance guided wave imaging in a quasi-isotropic composite plate," Smart Materials and Structures, vol. 20, No. 2, 9 pages.

(Continued)

*Primary Examiner* — Laura Martin
*Assistant Examiner* — Rose M Miller
(74) *Attorney, Agent, or Firm* — Yee & Associates, P.C.

(57) ABSTRACT

A method and apparatus for identifying an inconsistency. A number of waves that propagate through a structure are generated. A response signal is generated in response to detecting at least a portion of the number of waves that propagate through the structure. A determination is made as to whether the response signal includes a reflected component. A presence of the inconsistency in the structure is indicated when the response signal includes the reflected component.

19 Claims, 11 Drawing Sheets

(56) References Cited

OTHER PUBLICATIONS

Santoni et al., "Lamb wave-mode tuning of piezoelectric wafer active sensors for structural health monitoring," Transactions of the ASME, vol. 129, Dec. 2007, pp. 752-762.

Extended European Search Report, regarding Application No. 12191258.8, dated Aug. 13, 2014, 5 pages.

Bourasseau et al., "Radome health monitoring with Lamb waves; experimental approach," NDT & E International, vol. 33, No. 6, Sep. 2000, pp. 393-400.

Kim et al., "Damage assessment in layered composites using spectral analysis and Lamb wave," Composites Part B: Engineering, vol. 38, Issues 7-8, Oct.-Dec. 2007, pp. 800-809.

Kim et al., "Instantaneous reference-free crack detection based on polarization characteristics of piezoelectric materials," Smart Materials and Structures, vol. 16, No. 6, Oct. 2007, pp. 2375-2387.

Koh et al., "Effects of local stiffness changes and delamination on Lamb wave transmission using surface-mounted piezoelectric transducers," Composite Structures, vol. 57, Issues 1-4, Jul. 2002, pp. 437-443.

Lemistre et al., "Structural health monitoring system based on diffracted Lamb wave analysis by multiresolution processing," Smart Materials and Structures, vol. 10, No. 3, pp. 504-511.

Su et al., "A damage identification technique for CF/EP composite laminates using distributed piezoelectric transducers," Composite Structures, vol. 57, Issues 1-4, Jul. 2002, pp. 465-471.

Su et al., "Selective generation of Lamb wave modes and their propagation characteristics in defective composite laminates," Proceedings of the Institute of Mechanical Engineers, Part L: Journal of Materials Design and Application, vol. 218, Apr. 2004, pp. 95-110. (Abstract only).

Yeum et al., "Lamb wave mode decomposition using concentric ring and circular piezoelectric transducers," Wave Motion, vol. 48, Issue 4, Jun. 2011, pp. 358-370.

Wang et al., "Damage detection using piezoelectric transducers and the Lamb wave approach: I System analysis," Smart Materials and Structures, vol. 17, No. 2, Apr. 2008, pp. 1-15.

Kessler et al., "Damage Detection in Composite Materials Using Lamb Wave Methods," Smart Materials and Structures, vol. 11, No. 2, Apr. 2002, pp. 1-24.

\* cited by examiner

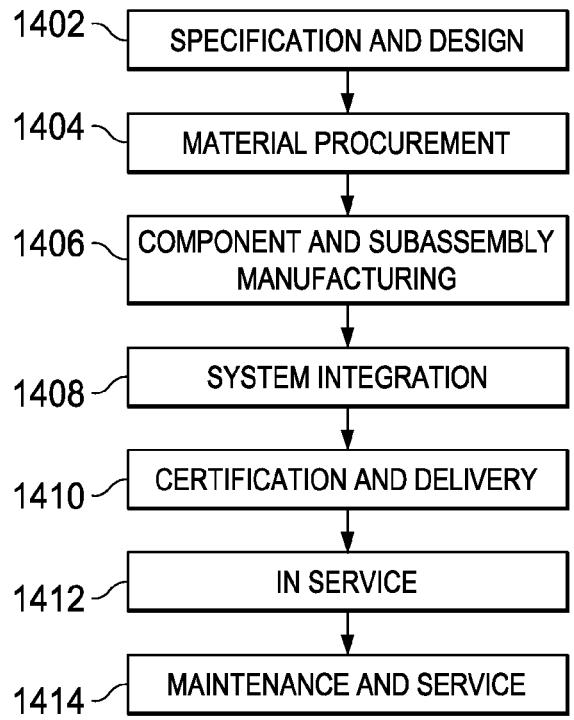
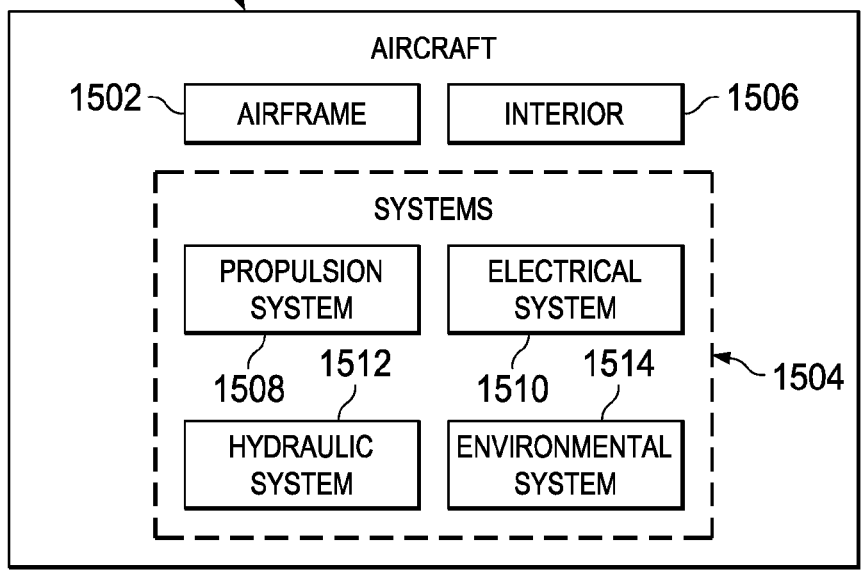

REFERENCE FREE INCONSISTENCY DETECTION SYSTEM

BACKGROUND INFORMATION

1. Field

The present disclosure relates generally to detecting inconsistencies in structures and, in particular, to detecting inconsistencies in structures using waves transmitted through the structures.

2. Background

Composite and metallic aircraft structures may be susceptible to internal changes that may occur from different events. These events may include fatigue, impacts, mechanical stresses, electromagnetic effects, and other changes. These changes may occur suddenly or may occur over time. In some cases, these changes may be undesirable. Undesirable changes in aircraft structures are referred to as inconsistencies.

An aircraft may be inspected to determine whether inconsistencies have developed in structures in the aircraft. These inspections may be performed periodically or after visual indications reveal that inconsistencies may be present. Inconsistencies may occur from operations such as cargo loading and unloading. Other inconsistencies may occur through an unintended contact of a vehicle with an aircraft.

Inspections of the aircraft are time consuming and costly. These inspections reduce the time that an aircraft is available for flights. As a result, losses in revenue may occur when an aircraft is out of service for inspection.

The time that an aircraft is out of service may be reduced through the use of health monitoring systems. Health monitoring systems may be used to determine whether changes have occurred to structures in the aircraft without requiring the aircraft to be taken out of service. By having health monitoring systems built into, or associated with, the structures in an aircraft, these systems may monitor the structures during operation of the aircraft.

Health monitoring systems may employ ultrasonic testing. Ultrasonic testing involves using transducers to scan a structure in the aircraft. These transducers may function as transmitters and sensors. These transducers may be mounted on the surface of a structure or embedded in the structure. Transducers functioning as transmitters may generate waves that propagate into the structure. Transducers functioning as sensors detect the waves transmitted into the structure by the transmitters.

Typically, these detected waves are analyzed by the health monitoring system to determine whether inconsistencies may be present. A response signal generated in response to detecting waves propagating through a structure may be compared to signals for a baseline for the structures. The signals for the baseline are generated when the structures in the aircraft do not have inconsistencies. The comparison of the response signal with the signals for the baseline is used to determine whether inconsistencies may be present.

Structures, however, may change over time even though inconsistencies that are undesirable may not be present. As a result, comparison between response signals and baseline signals may not be as effective because, over time, the baseline may become more and more different from response signals generated by the health monitoring system.

As a result, a health monitoring system may indicate a presence of an inconsistency even though one is not present. A new baseline may need to be generated for the structure. Generating a new baseline for the structure may be time-consuming. Additionally, in generating a new baseline, additional time and expense may be needed to perform other testing to ensure that inconsistencies are not present in the structures for which the new baseline is created.

Therefore, it would be desirable to have a method and apparatus that takes into account at least some of the issues discussed above as well as possibly other issues.

SUMMARY

In one illustrative embodiment, a method is provided for identifying an inconsistency. A number of waves that propagate through a structure are generated. A response signal is generated in response to detecting at least a portion of the number of waves that propagate through the structure. A determination is made as to whether the response signal includes a reflected component. A presence of the inconsistency in the structure is indicated when the response signal includes the reflected component.

In another illustrative embodiment, an apparatus comprises a transducer system and an analyzer. The transducer system is configured to be associated with a structure. The transducer system is configured to generate a number of waves that propagate through the structure and generate a response signal in response to detecting at least a portion of the number of waves that propagate through the structure. The analyzer is configured to control the transducer system to receive the response signal from the transducer system. The analyzer is also configured to determine whether the response signal includes a reflected component. Further, the analyzer is configured to indicate a presence of an inconsistency in the structure when the response signal includes the reflected component.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and features thereof will best be understood by reference to the following detailed description of an illustrative embodiment of the present disclosure when read in conjunction with the accompanying drawings, wherein:

FIG. 14 is an illustration of an aircraft manufacturing and service method in accordance with an illustrative embodiment; and FIG. 15 is an illustration of an aircraft in which an illustrative embodiment may be implemented.

DETAILED DESCRIPTION

Figure 1:
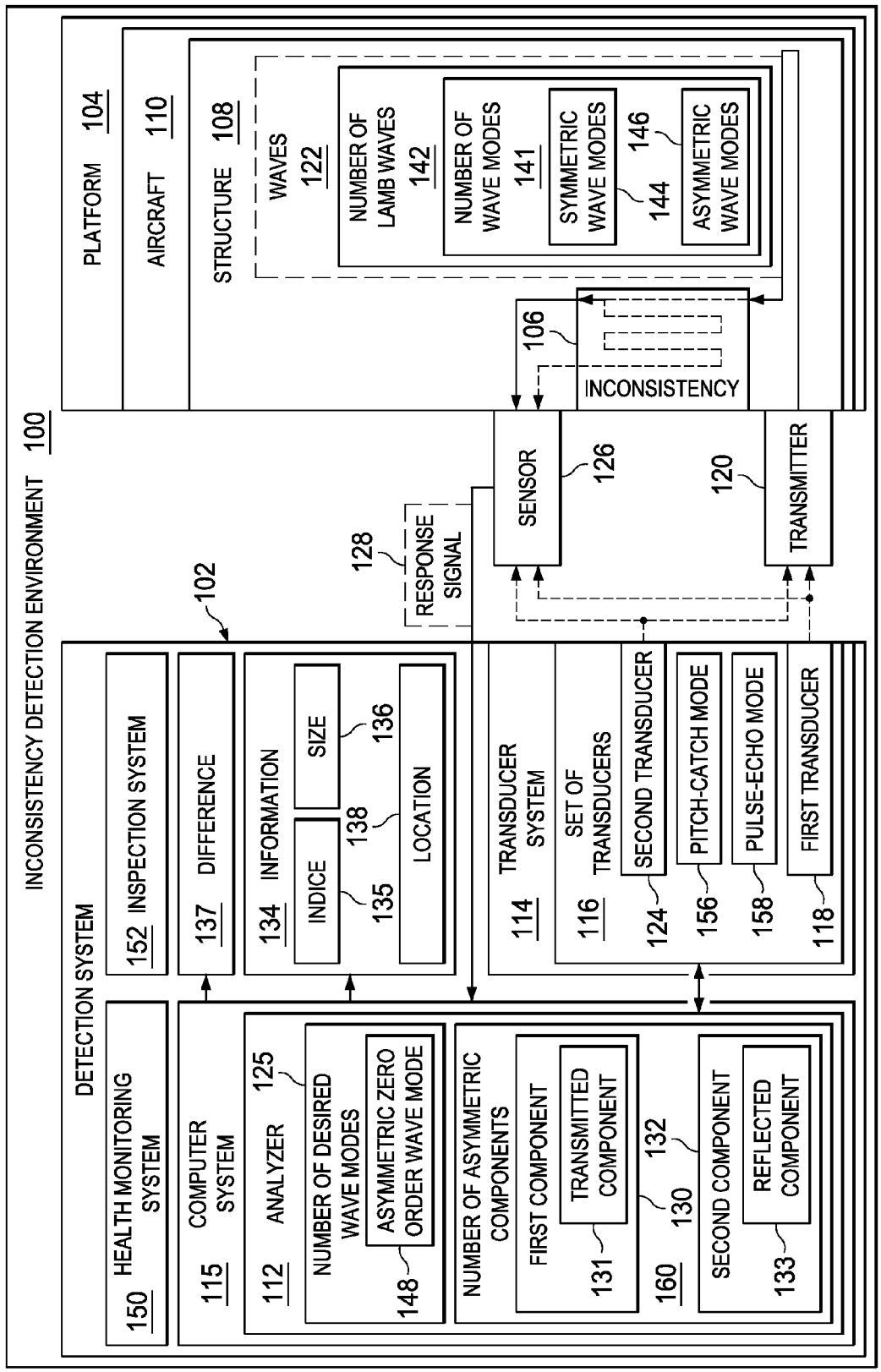
FIG. 1 is an illustration of an inconsistency detection environment in the form of a block diagram in accordance with an illustrative embodiment.

With reference now to FIG. 1, an illustration of an inconsistency detection environment in the form of a block diagram is depicted in accordance with an illustrative embodiment. Inconsistency detection environment 100 includes detection system 102. Detection system 102 may be used to detect inconsistency 106 in platform 104. As depicted, inconsistency 106 may be present in structure 108 in platform 104. Platform 104 is aircraft 110 in this depicted example.

Detection system 102 includes analyzer 112 and transducer system 114. In the illustrative examples, analyzer 112 may be implemented using hardware, software, or a combination of the two. In these illustrative examples, analyzer 112 may be implemented in computer system 115. Computer system 115 is a number of computers. A "number" as used herein with reference to items, means one or more items. For example, a number of computers may be one or more computers. When more than one computer is present in computer system 115, these computers may be in communication with each other over a network.

In the illustrative examples, transducer system 114 is implemented using hardware. More specifically, transducer system 114 includes set of transducers 116. As used herein, a "set of" items means one or more items. For example, set of transducers 116 may include one or more transducers. As one illustrative example, set of transducers 116 may include one or more piezoelectric transducers.

As depicted, transducer system 114 is associated with platform 104. When a first component, such as transducer system 114, is associated with a second component, such as platform 104, the association is a physical association in these depicted examples.

For example, the first component may be considered to be associated with the second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

When analyzer 112 and transducer system 114 are associated with platform 104 and operate during operation of platform 104, detection system 102 takes the form of health monitoring system 150. When detection system 102 is used during maintenance or in between operation of platform 104, detection system 102 takes the form of inspection system 152.

In these illustrative examples, analyzer 112 controls the operation of set of transducers 116 in transducer system 114. For example, analyzer 112 may control whether a transducer in set of transducers 116 is configured to operate as transmitter 120 to generate waves, sensor 126 to detect waves, or as a combination of the two.

As one illustrative example, set of transducers 116 may include first transducer 118 and second transducer 124. Analyzer 112 may control whether first transducer 118 operates as transmitter 120, sensor 126, or a combination of the two. Further, analyzer 112 may control whether second transducer 124 operates as transmitter 120, sensor 126, or a combination of the two.

The configuration of set of transducers 116 in transducer system 114 depends on a mode of operation for transducer system 114. For example, transducer system 114 may be configured to operate in pitch-catch mode 156, pulse-echo mode 158, some other suitable mode, or a combination thereof.

When pitch-catch mode 156 is used for set of transducers 116, first transducer 118 in set of transducers 116 is configured to operate as transmitter 120. Further, second transducer 124 may be configured to operate as sensor 126. In pitch-catch mode 156, first transducer 118 generates waves 122 that propagate through structure 108. Second transducer 124 is configured to detect at least a portion of waves 122 that propagate through structure 108. Further, second transducer 124 generates response signal 128 in response to detecting at least a portion of waves 122 that propagate through structure 108.

In other illustrative examples, set of transducers 116 may be configured to operate in pulse-echo mode 158. When pulse-echo mode 158 is used for set of transducers 116, a same transducer may be configured to operate as both a transmitter and a sensor. For example, first transducer 118 may be configured to operate as transmitter 120 and sensor 126. First transducer 118 may generate waves 122 that propagate through structure 108. Further, first transducer 118 may detect at least a portion of waves 122 that propagate through structure 108 and as a result may generate response signal 128. As another example, second transducer 124 may be configured to operate as transmitter 120 and sensor 126.

In these illustrative examples, waves 122 may take the form of number of Lamb waves 142. In particular, the transducer in set of transducers 116 that is configured to function as transmitter 120 may excite number of Lamb waves 142 in structure 108. A Lamb wave is an elastic guided wave that propagates through a solid structure. The solid structure may be, for example, a solid plate. Typically, the particle motion for a Lamb wave lies in the plane that contains the direction of wave propagation for the Lamb wave and a direction perpendicular to the plate.

In generating number of Lamb waves 142, the transducer that functions as transmitter 120 is controlled to excite number of wave modes 141 for number of Lamb waves 142. Each wave mode in number of wave modes 141 is a mode of vibration for number of Lamb waves 142. Number of wave modes 141 may include one or more of symmetric wave modes 144 and/or one or more asymmetric wave modes 146. Symmetric wave modes 144 may be substantially symmetrical about a centerline of the plane in which number of Lamb waves 142 lie. Asymmetric wave modes 146 may be asymmetrical around the centerline of the plane in which number of Lamb waves 142 lie.

The wave modes in number of wave modes 141 that are excited depend on the frequencies at which the transducers in set of transducers 116 operate. The frequencies at which the transducers in set of transducers 116 operate may be controlled by analyzer 112 in these illustrative examples. In this manner, analyzer 112 may control which of symmetric wave modes 144 and/or asymmetric wave modes 146 for number of Lamb waves 142 are excited and propagate through structure 108.

In one illustrative example, analyzer 112 controls set of transducers 116 to operate at frequencies in which number of Lamb waves 142 does not include modes other than number of desired wave modes 125. In these illustrative examples, number of desired wave modes 125 includes one wave mode in asymmetric wave modes 146. Asymmetric wave modes 146 for number of Lamb waves 142 are of interest for analysis by analyzer 112. Asymmetric wave modes 146 may be affected more by the presence of inconsistency 106 in structure 108 as compared to symmetric wave modes 144.

In particular, the velocities of asymmetric wave modes 146 may be reduced when these wave modes encounter inconsistency 106 as compared to the velocities for symmetric wave modes 144. Additionally, asymmetric wave modes 146 may be more sensitive to inconsistencies in the form of, for example, delamination, as compared to symmetric wave modes 144. In these illustrative examples, the asymmetric wave mode of interest is asymmetric zero order wave mode 148.

A zero order wave mode, such as asymmetric zero order wave mode 148, may be present over substantially the entire frequency spectrum. In other words, a zero order wave mode may be present over frequencies from substantially zero to infinity. However, a higher order wave mode may be present only at frequencies substantially at and above a resonant frequency of the plates. A higher order wave mode may include some other higher order wave mode. As a result, a zero order wave mode may carry more energy than a higher order wave.

Further, at frequencies below the resonant frequency of the first order wave mode, the zero order wave mode may only exist in asymmetric wave modes 146. Analysis and interpretation of a single order wave mode may be less time-consuming and less difficult than analysis and interpretation of multiple wave modes and/or higher order wave modes. In this manner, analysis of the information provided by asymmetric zero order wave mode 148 may be less time-consuming and complicated as compared to analysis of the information provided by both asymmetric zero order wave mode 148 and other higher order wave modes.

The transducer configured to function as sensor 126 may detect at least a portion of number of Lamb waves 142 that propagate through structure 108 and generate response signal 128. At least a portion of number of Lamb waves 142 may be one, some, or all of number of Lamb waves 142 that propagate through structure 108. Analyzer 112 may receive response signal 128 for processing.

Analyzer 112 may be configured to process a portion of response signal 128 generated by second transducer 124 that is measured for a selected period of time. This selected period of time may be selected such that waves reflected off of the boundaries or edges of structure 108 are not represented in the portion of response signal 128 processed.

Analyzer 112 processes the selected portion of response signal 128 to identify the number of components of the selected portion of response signal 128 that correspond to number of desired wave modes 125 for number of Lamb waves 142. In some cases, these "components" may be referred to as wave packets.

In particular, analyzer 112 may identify number of asymmetric components 160 in response signal 128. In other words, analyzer 112 may decompose the selected portion of response signal 128 into number of asymmetric components 160. As used herein, an "asymmetric component" may be a portion of response signal 128 that corresponds to at least one of asymmetric wave modes 146 in number of wave modes 141 for number of Lamb waves 142 that propagate through structure 108.

When inconsistency 106 is present in structure 108, analyzer 112 may identify first component 130 and second component 132 in number of asymmetric components 160 in response signal 128. In other words, analyzer 112 may decompose number of asymmetric components 160 into first component 130 and second component 132.

First component 130 may be transmitted component 131. Transmitted component 131 may be the portion of response signal 128 that corresponds to the portion of number of Lamb waves 142 that is not reflected within the area in structure 108 at which inconsistency 106 is located. In other words, transmitted component 131 corresponds to the portion of number of Lamb waves 142 that propagates through structure 108 without being reflected by inconsistency 106.

Further, analyzer 112 may determine whether second component 132 is reflected component 133. As used herein, a "reflected component" is a portion of response signal 128 that corresponds to the portion of number of Lamb waves 142 that is reflected within the area in structure 108 at which inconsistency 106 is located. In other words, reflected component 133 corresponds to the portion of number of Lamb waves 142 that bounces or is reflected within inconsistency 106 in structure 108 prior to being detected by sensor 126.

Analyzer 112 may determine that second component 132 is reflected component 133 when second component 132 is received after first component 130 in response signal 128 and when second component 132 is more dispersive than first component 130. Second component 132 is more dispersive than first component 130 when second component 132 is wider than first component 130 in response signal 128 with respect to the time domain. In other words, the portion of number of Lamb waves 142 that corresponds to second component 132 may extend over a longer period of time as compared to the portion of number of Lamb waves 142 that corresponds to first component 130.

In these illustrative examples, reflected component 133 may not be present when inconsistency 106 is not present in structure 108. Further, in some cases, second component 132 may not be identified in number of asymmetric components 160 when inconsistency 106 is not present in structure 108. In other words, number of asymmetric components 160 extracted from response signal 128 may only include first component 130 when inconsistency 106 is not present in structure 108.

Further, in these illustrative examples, analyzer 112 identifies difference 137. Difference 137 is a difference between the arrival time of transmitted component 131 and the arrival time of reflected component 133. Difference 137 may be used to identify whether inconsistency 106 is present as well as identify other information in these illustrative examples.

With a detection of inconsistency 106, information 134 about inconsistency 106 may be identified. Information 134 may include, for example, at least one of indice 135, size 136, location 138, and other suitable information about inconsistency 106. In these illustrative examples, size 136 may be described using dimensions. Location 138 may be a location based on aircraft coordinates for aircraft 110.

Indice 135 provides a value for inconsistency 106. Indice 135 is used in the illustrative examples to indicate a severity of inconsistency 106 relative to other inconsistencies that may occur.

In the illustrative examples, the detection of inconsistency 106 and the identification of information 134 for inconsistency 106 may be performed without needing prior information about structure 108. In other words, a baseline of signals for structure 108 may be unnecessary with the use of detection system 102.

Further, detection system 102 may identify inconsistency 106 under varying operation and environmental conditions. As a result, fewer false positives may be present with changes in structure 108 that may not result in inconsistency 106 over time when reference information about structure 108 is not used.

The illustration of inconsistency detection environment 100 in FIG. 1 is not meant to imply physical or architectural limitations to the manner in which an illustrative embodiment may be implemented. Other components in addition to and/or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative examples, analyzer 112 may be located on another platform from transducer system 114. Transducer system 114 may send response signal 128 to analyzer 112 over a communications link, such as a wireless communications link.

In other illustrative examples, each transducer in set of transducers 116 may be controlled by a processor unit associated with the transducer in addition to and/or in place of analyzer 112. For example, without limitation, a processor unit associated with first transducer 118 may control the frequency at which first transducer 118 operates instead of analyzer 112. Of course, in still other illustrative examples, at least a portion of analyzer 112 may be implemented in each of set of transducers 116.

Further, although the example has been described with respect to platform 104 taking the form of aircraft 110, the illustrative embodiment may be applied to other types of platforms. For example, without limitation, other illustrative embodiments may be applied to a mobile platform, a stationary platform, a land-based structure, an aquatic-based structure, a space-based structure and/or some other suitable object. More specifically, the different illustrative embodiments may be applied to, for example, without limitation, a submarine, a bus, a personnel carrier, a tank, a train, an automobile, a spacecraft, a space station, a satellite, a surface ship, a power plant, a dam, a manufacturing facility, a building, and/or some other suitable object.

Figure 2:
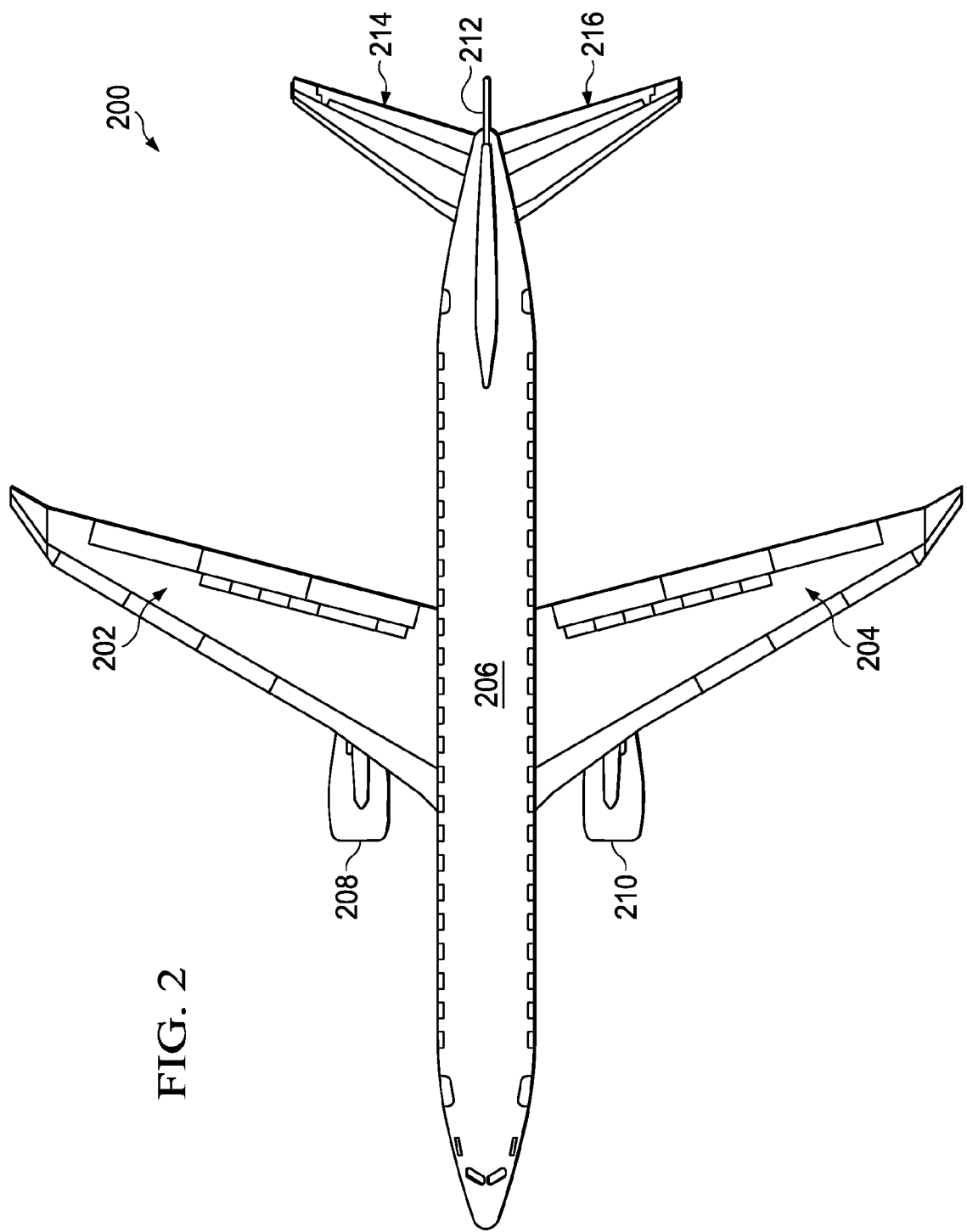
FIG. 2 is an illustration of an aircraft in accordance with an illustrative embodiment.

With reference next to FIG. 2, an illustration of an aircraft is depicted in accordance with an illustrative embodiment. Aircraft 200 is an example of a physical implementation of aircraft 110 shown in block form in FIG. 1.

In this illustrative example, aircraft 200 has wing 202 and wing 204 attached to fuselage 206. Additionally, engine 208 is attached to wing 202 and engine 210 is attached to wing 204. Further, aircraft 200 has vertical stabilizer 212 and horizontal stabilizers 214 in tail section 216.

In these illustrative examples, detection system 102 in FIG. 1 may be associated with aircraft 200. For example, set of transducers 116 in transducer system 114 in FIG. 1 may be associated with structures in wing 202 and wing 204, as well as fuselage 206. Also, set of transducers 116 may be associated with vertical stabilizer 212, horizontal stabilizers 214, or a combination thereof. Set of transducers 116 also may be associated with structures in engine 208 and engine 210. Set of transducers 116 may be placed on the surface of structures, embedded in structures, or otherwise associated with structures in aircraft 200.

In this manner, more accurate detection of inconsistencies of aircraft 200 may occur with the use of detection system 102 in aircraft 200. The monitoring of different structures in aircraft 200 may be performed during operation of aircraft 200 without the use of a baseline of signals for aircraft 200 in FIG. 2.

Figure 3:
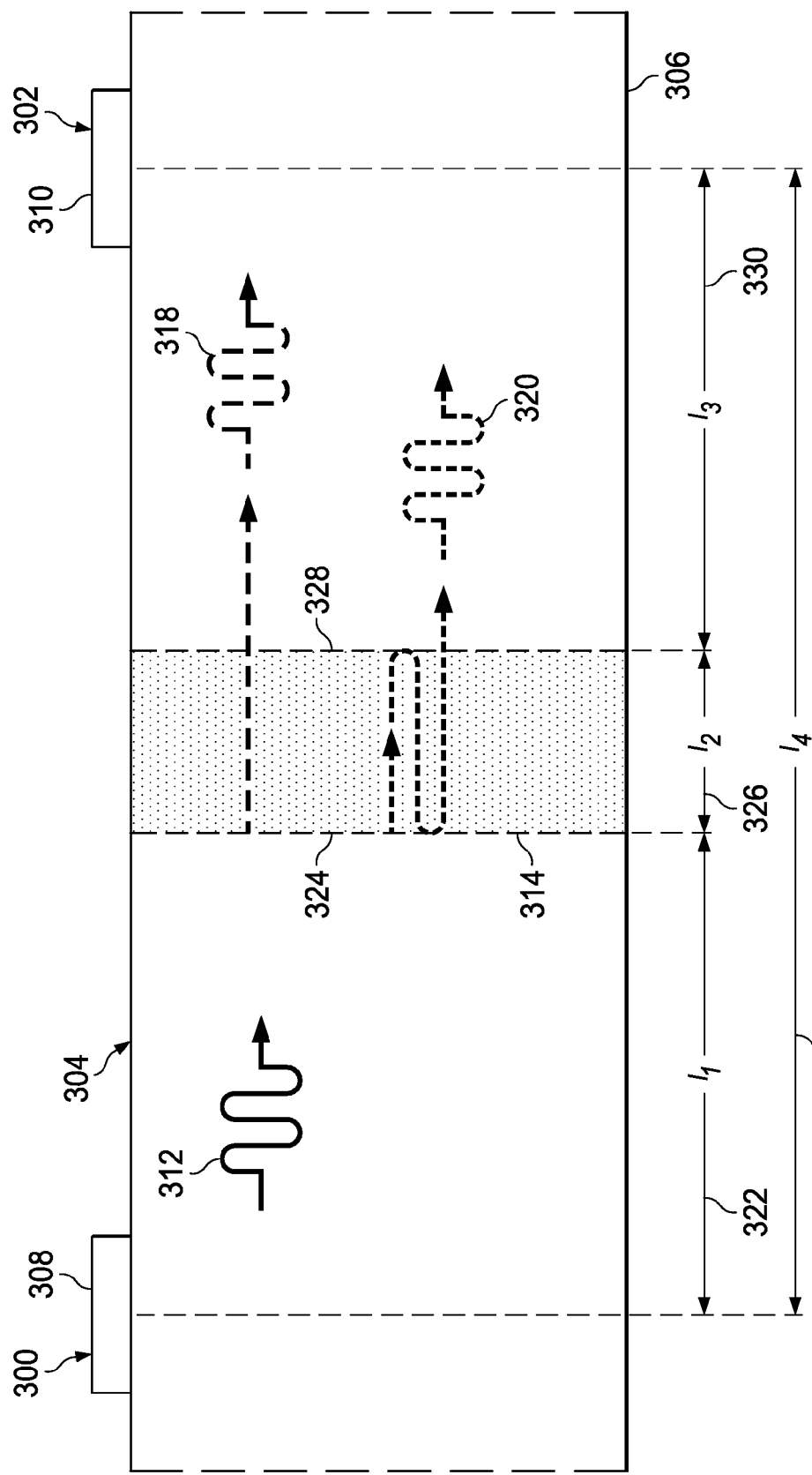
FIG. 3 is an illustration of waves generated and detected by transducers for identifying an inconsistency in accordance with an illustrative embodiment.

Turning next to FIG. 3, an illustration of waves generated and detected by transducers for identifying an inconsistency is depicted in accordance with an illustrative embodiment. Identifying an inconsistency may include detecting the inconsistency, identifying information about the inconsistency, or both. In this illustrative example, first transducer 300 and second transducer 302 are associated with structure 304. In this example, structure 304 is a structure in aircraft 200.

As depicted, first transducer 300 and second transducer 302 are located on surface 306 of structure 304. Of course, in other illustrative examples, first transducer 300 and second transducer 302 may be embedded within structure 304.

First transducer 300 is configured to function as transmitter 308 and second transducer 302 is configured to function as sensor 310. In this illustrative example, transmitter 308 and sensor 310 are in pitch-catch configuration. In other words, transmitter 308 generates waves that propagate through structure 304 and sensor 310 detects at least a portion of these waves that propagate through structure 304. These waves may be Lamb waves.

For example, transmitter 308 generates number of waves 312 that propagate through structure 304. Number of waves 312 may include an asymmetric zero order wave mode in this example. At least a portion of number of waves 312 that propagate through structure 304 travel towards sensor 310. Further, in this illustrative example, at least a portion of number of waves 312 travels through inconsistency 314 in structure 304.

As depicted, the portion of number of waves 312 that travels through inconsistency 314 and that is detected by sensor 310 includes transmitted portion 318 and reflected portion 320. Transmitted portion 318 of number of waves 312 may be in the asymmetric zero order wave mode and may pass through inconsistency 314 without being reflected between first boundary 324 and second boundary 328 of inconsistency 314. Reflected portion 320 of number of waves 312 also may be in the asymmetric zero order wave mode and may be reflected at second boundary 328 and first boundary 324 of inconsistency 314 as reflected portion 320 passes through inconsistency 314. Reflected portion 320 may bounce between second boundary 328 and first boundary 324 any number of times.

Sensor 310 may generate a response signal as sensor 310 detects the portion of number of waves 312 that travel towards sensor 310. Sensor 310 may detect reflected portion 320 after transmitted portion 318 is detected. The components of this response signal that correspond to transmitted portion 318 and reflected portion 320 of number of waves 312 may be processed and analyzed to detect a presence of inconsistency 314 and identify information about inconsistency 314.

In this illustrative example, length L1 322 is the distance from transmitter 308 to first boundary 324 of inconsistency 314. Length L2 326 is the length of inconsistency 314. Length L2 326 is the distance between first boundary 324 and second boundary 328 of inconsistency 314. Length L3 330 is the distance from second boundary 328 of inconsistency 314 to sensor 310. Length L4 332 is the distance from transmitter 308 to sensor 310.

The components of the response signal generated by sensor 310 that correspond to transmitted portion 318 and reflected portion 320 of number of waves 312 may be processed and analyzed to identify a range of possible values for length L2 326 for inconsistency 314.

Further, in these depicted examples, additional information about inconsistency 314 may be identified using a difference between the arrival time of transmitted portion 318 and the arrival time of reflected portion 320 at sensor 310. This difference in arrival times is represented as Δt in these illustrative examples.

The difference in arrival times, Δt, may be represented as follows:

$$\Delta t = \frac{2l_2}{v_d} = \frac{2l_2}{\xi \lambda_d}$$

where $\xi$ is the frequency for the asymmetric zero order wave mode for number of waves 312 generated by transmitter 308, $\lambda_d$ is the wavelength for the asymmetric zero order wave mode, and $l_2$ is length L2 326. This frequency, $\xi$, may be referred to as a central frequency.

The difference in arrival times, Δt, may be used to identify additional information about inconsistency 314 such as, for example, without limitation, an indice for inconsistency 314, a size of inconsistency 314, a location of inconsistency 314, and other information. The indice for inconsistency 314 may be an m value for inconsistency 314. This m value is non-dimensional and indicates a stiffness of the material in structure 304 in these illustrative examples. This stiffness is a relative change from other areas in structure 304 in which inconsistency 314 is not present.

The m value may be identified using the central frequency, $\xi$, and the difference in arrival times, Δt. More specifically, the m value may be identified as follows:

$$m = \frac{l_2}{\lambda_d} = \frac{\xi \Delta t}{2}$$

where m is the m value. Additionally, the size of inconsistency 314 also may be identified. In this illustrative example, the size of inconsistency 314 may be a one-dimensional size, length L2 326. When a value for m is identified, length L2 326 also may be identified from the equation above using the m value.

The m value represents the possible combinations of values for length L2 326 and $\lambda_d$, which is a ratio of $v_d$ to $\xi$. In other words, the wavelength, $\lambda_d$, for the asymmetric zero order wave mode for number of waves 312 is a ratio of the velocity for the asymmetric zero order wave mode for number of waves 312 traveling through inconsistency 314 to the central frequency, $\xi$. In these illustrative examples, the value for $\lambda_d$ is directly related to the degree or severity of inconsistency 314. This relationship is present because a lower velocity results from the reduced effective material stiffness present within inconsistency 314. Thus, identifying m allows length L2 326 and the degree of inconsistency 314 represented by velocity reduction to be estimated.

In these illustrative examples, the possible maximum length L2 326 of inconsistency 314 may be estimated using the following equations:

$$v_i = \frac{l - l_2}{t - t_d} = \frac{l}{t - t_i} - \frac{l_2}{t - t_d}, v_d = \frac{l_2}{t_d},$$

where $v_i$ is the velocity of the asymmetric zero order wave mode for the portion of number of waves 312 that propagates through an area in structure 304 in which inconsistency 314 is not present, $v_d$ is the velocity of the asymmetric zero order wave mode for the portion of number of waves 312 that propagates through inconsistency 314, t is the arrival time of transmitted portion 318, $\square$ is length L4 332, L2 is length L2 326 of inconsistency 314, and $t_d$ is half of the difference between the time of arrival of transmitted portion 318 and reflected portion 320. In other words, $t_d$ is half the difference in arrival times, Δt.

The presence of inconsistency 314 causes a reduction in the effective stiffness of the area in structure 304 at which inconsistency 314 is located. This reduction in effective stiffness, in turn, causes a reduction in the velocity of the portion of number of waves 312 that travel through inconsistency 314. As a result, an assumption may be made that $v_d$ is less than $v_i$.

With this assumption, the range of possible values for the length L2 326 of inconsistency 314 may be estimated as follows:

$$\frac{l_2}{t_d} < \frac{l}{t - t_d} - \frac{l_2}{t - t_d},$$

$$0 < l_2 < l\frac{t_d}{t} \text{ (lower bound is 0).}$$

In particular, a lower limit and an upper limit for the range of possible values for length L2 326 may be estimated. Length L2 326 may be estimated as greater than about zero and less than about $$l\frac{t_d}{t}.$$

Figure 4:
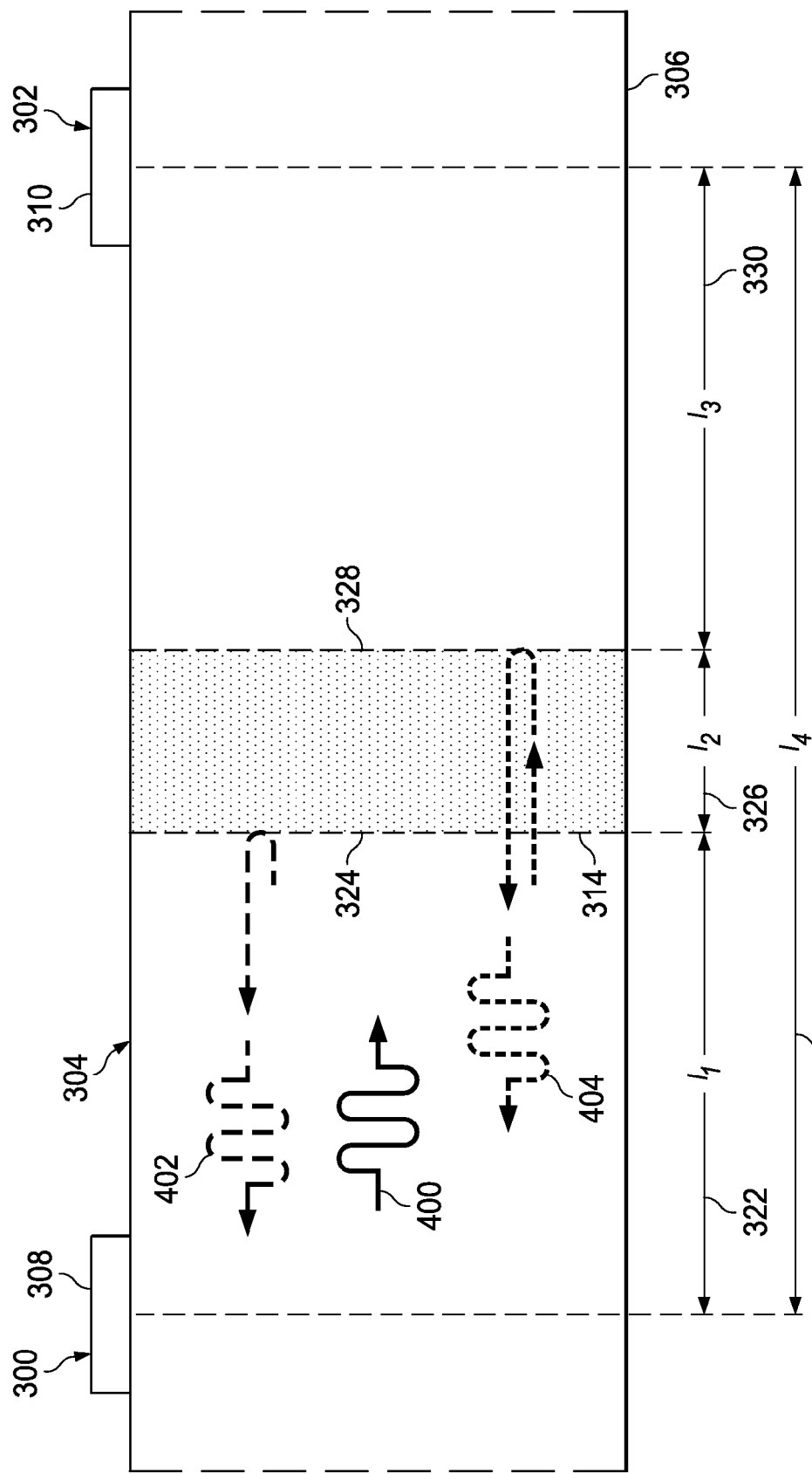
FIG. 4 is an illustration of waves generated and detected by a transducer in accordance with an illustrative embodiment.

Turning next to FIG. 4, an illustration of waves generated and detected by a transducer is depicted in accordance with an illustrative embodiment. In this illustrative example, first transducer 300 is in a pulse-echo configuration and functions as both a transmitter and a sensor.

First transducer 300 generates first number of waves 400 that propagate through structure 304. First number of waves 400 may be a number of Lamb waves of the asymmetric zero order wave mode. In this illustrative example, first portion 402 and second portion 404 of first number of waves 400 are received by first transducer 300.

First portion 402 may be the portion of first number of waves 400 that is reflected off of first boundary 324 without encountering inconsistency 314. First portion 402 may be referred to as a transmitted portion since first portion 402 does not pass through inconsistency 314 and is not reflected within inconsistency 314.

Second portion 404 may be the portion of first number of waves 400 that is reflected off of second boundary 328. In particular, second portion 404 may the portion of first number of waves 400 that travels through inconsistency 314 and is reflected off of second boundary 328.

Figure 5:
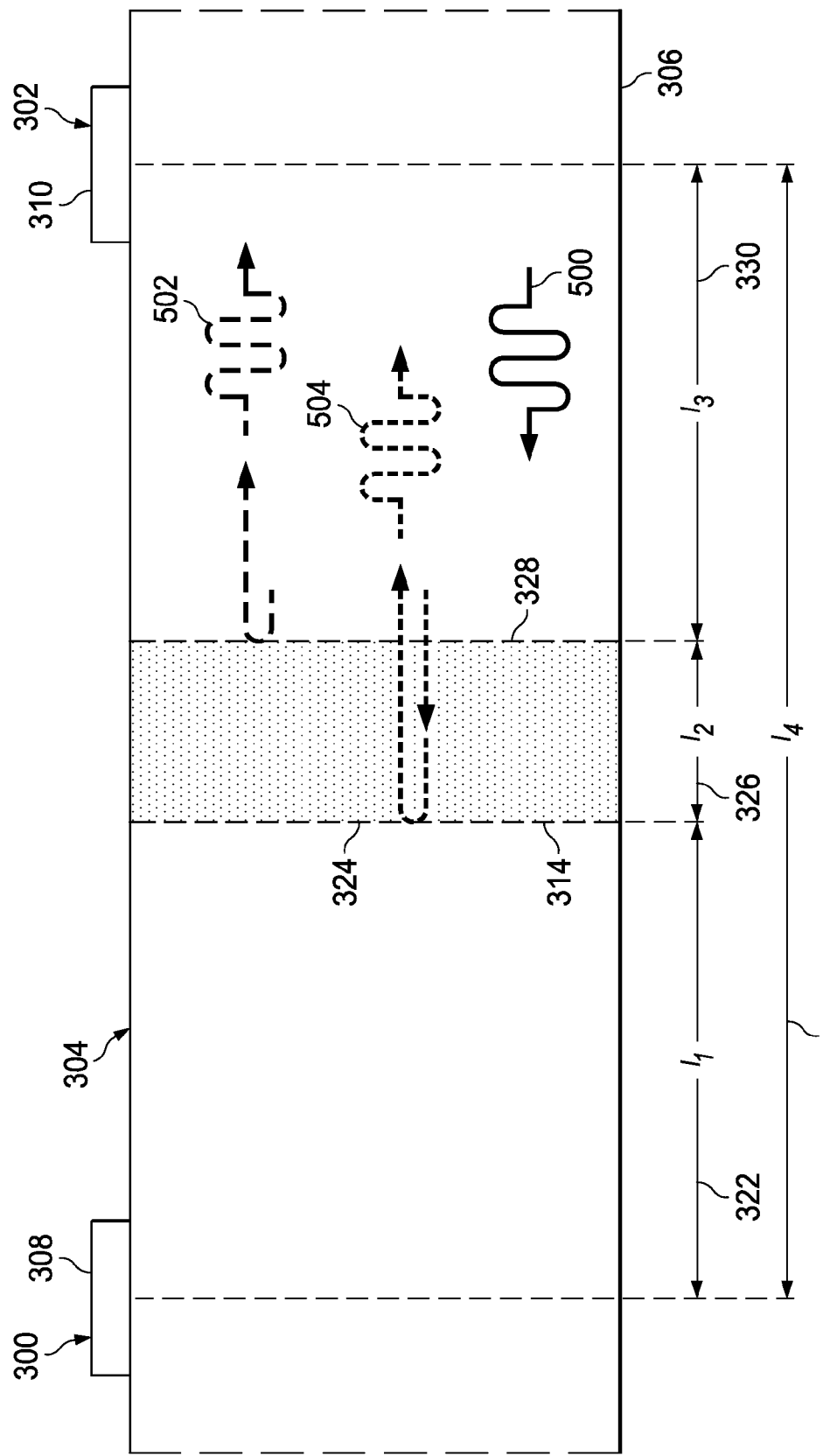
FIG. 5 is an illustration of waves generated and detected by a transducer in accordance with an illustrative embodiment.

In FIG. 5, an illustration of waves generated and detected by a transducer is depicted in accordance with an illustrative embodiment. In a similar fashion, second transducer 302 is in a pulse-echo configuration and functions as a sensor and transmitter. Second transducer 302 sends second number of waves 500 into structure 304. In response, third portion 502 and fourth portion 504 are detected by second transducer 302. Third portion 502 reflects off of second boundary 328. Fourth portion 504 reflects off of first boundary 324.

From the signals sent and received by first transducer 300 in FIG. 4 and second transducer 302 in FIG. 5, a range of possible values for length L2 326 of inconsistency 314 may be identified. Length L2 326 may be represented as follows:

$$l_2 = l - l_1 - l_3 = l - l_1 - l_1 \frac{t_3}{t_1} = l - l_1 \left( \frac{t - t_d}{t_1} \right),$$

where $\square$ is length L4 332, $\square_1$ is length L1 322, $t_1$ is the time for first number of waves 400 to reach first boundary 324, and $t_3$ is the time for second number of waves 500 to reach second boundary 328. As depicted, $t_1$ may be estimated from the time at which first number of waves 400 are generated and transmitted into structure 304 and the time at which first portion 402 is detected. For example, $t_1$ may be half of the time between the time at which first number of waves 400 are generated and transmitted into structure 304 and the time at which first portion 402 is detected. Similarly, $t_3$ is the time for second number of waves 500 to reach second boundary 328. In a manner similar to estimating $t_1$, $t_3$ may be estimated using the time at which second number of waves 500 are generated and transmitted into structure 304 and the time at which third portion 502 is detected.

As a result, an estimate for the range of possible values for the distance from first transducer 300 to first boundary 324 of inconsistency 314 may be made as follows:

$$0 < l - l_1 \left( \frac{t - t_d}{t_1} \right) < l \frac{t_d}{t}$$

$$l \frac{t_1}{t} < l_1 < l \left( \frac{t_1}{t - t_d} \right).$$

In this manner, a location of inconsistency 314 may be estimated.

As a result, with detection system 102, an identification of inconsistency 314 may be made. As described above, this identification includes detecting the presence of inconsistency 314 in structure 304 and identifying information about inconsistency 314. This information may include an identification of an m value indicating a value for the severity of inconsistency 314. Additionally, first boundary 324 and second boundary 328 may be identified. The locations of these boundaries may be identified relative to the locations of first transducer 300 and second transducer 302 after length L1 322, length L2 326, and length L3 330 are identified.

The illustrative examples in FIGS. 3-5 only estimate length L2 326 with first boundary 324 and second boundary 328 in one dimension. Additional dimensions may be identified in the same plane with additional transducers. With additional transducers in a grid or other suitable configuration, the overall boundary of inconsistency 314 may be identified. With the identification of the boundaries, a size may be identified for inconsistency 314. In this manner, the size of inconsistency 314 may be more accurately identified through multiple paths with multiple transducers.

Figure 6:
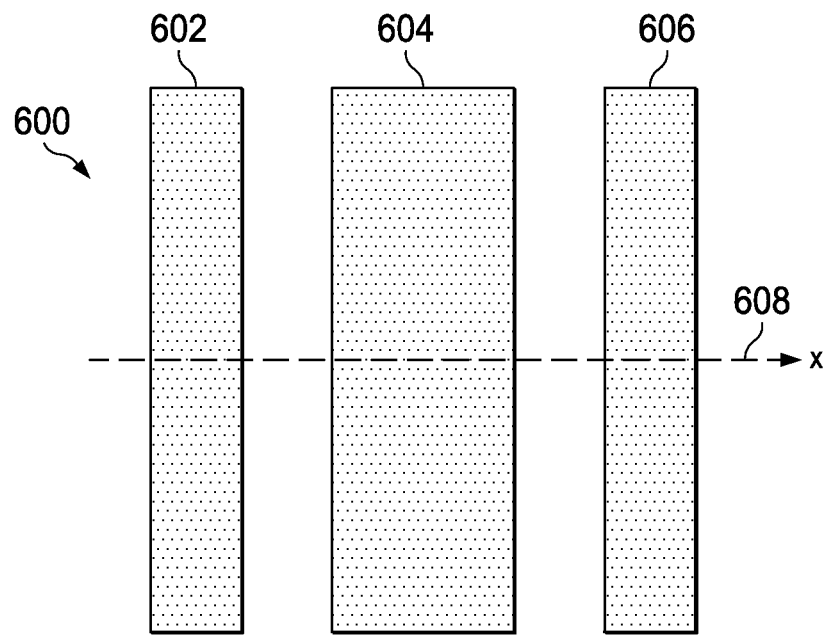
FIG. 6 is an illustration of a transducer in accordance with an illustrative embodiment.

Turning now to FIG. 6, an illustration of a transducer is depicted in accordance with an illustrative embodiment. Transducer 600 is shown from a top view and a side view in these illustrative examples. Transducer 600 is a segmented transducer having segments 602, 604, and 606. Arrow 608 illustrates a direction for mode decomposition that may be used with transducer 600.

Figure 7:
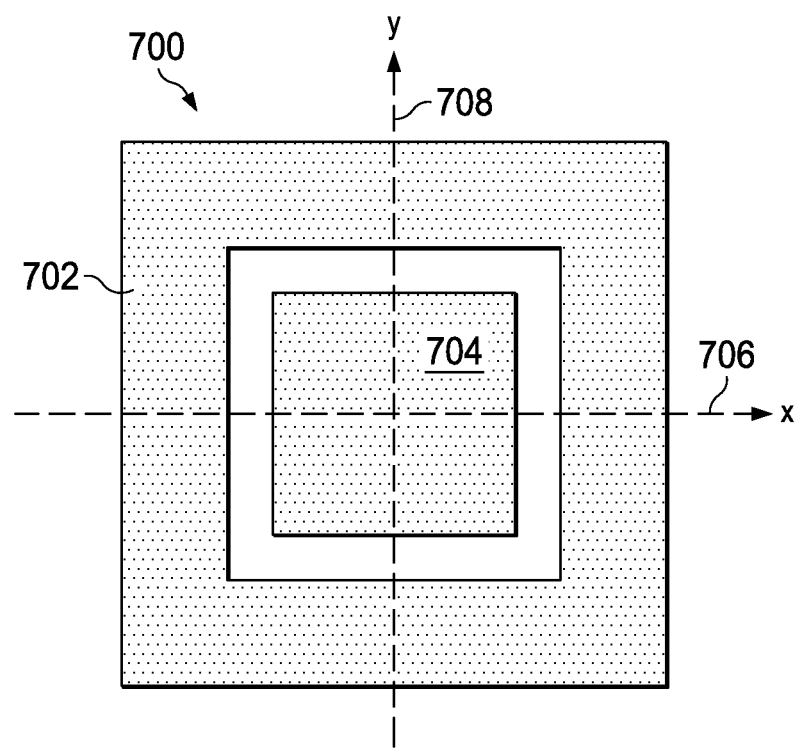
FIG. 7 is an illustration of another transducer in accordance with an illustrative embodiment.

Turning now to FIG. 7, an illustration of another transducer is depicted in accordance with an illustrative embodiment. In this illustrative example, transducer 700 is an example of another transducer that may be used to transmit and receive signals. Transducer 700 has segment 702 and segment 704. Mode decomposition may be performed in the direction of arrow 706 and arrow 708 in this illustrative example.

Figure 8:
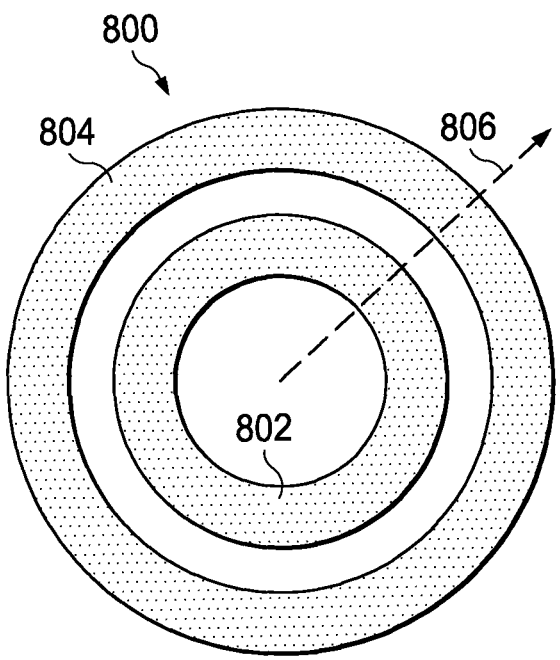
FIG. 8 is an illustration of another transducer in accordance with an illustrative embodiment.

Turning next to FIG. 8, an illustration of another transducer is depicted in accordance with an illustrative embodiment. In this illustrative example, transducer 800 is another multiple segment transducer that may be used to send signals, receive signals, or a combination of the two. In this depicted example, transducer 800 includes segment 802 and segment 804. Arrow 806 indicates a direction in which mode decomposition may be performed.

Figure 9:
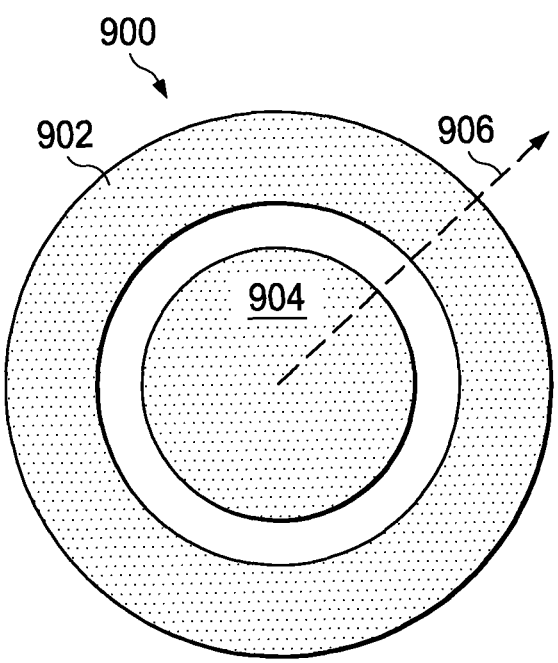
FIG. 9 is an illustration of another transducer in accordance with an illustrative embodiment.

Turning next to FIG. 9, an illustration of another transducer is depicted in accordance with an illustrative embodiment. Transducer 900 is a multiple segment transducer. Transducer 900 includes segment 902 and segment 904. Arrow 906 indicates a direction for which mode decomposition may be performed.

The use of transducers 600, 700, 800, and 900 in FIGS. 6-9 may be used to perform mode decomposition of signals at different frequencies. This decomposition of signals to obtain different modes may be performed without changing the size, spacing, configuration, or some combination thereof. Of course, other types of transducers also may be used. When non-segmented transducers are employed, parameters such as frequency, size of transducers, spacing configuration, and other parameters may be changed to obtain Lamb waves of the asymmetric zero order wave mode.

The illustrations of the different components in FIGS. 3-9 may be combined with components in FIG. 1, used with components in FIG. 1, or a combination of the two. Additionally, some of the components illustrated in FIGS. 3-9 may be illustrative examples of how a component shown in block form in FIG. 1 may be implemented as a physical structure.

Figure 10:
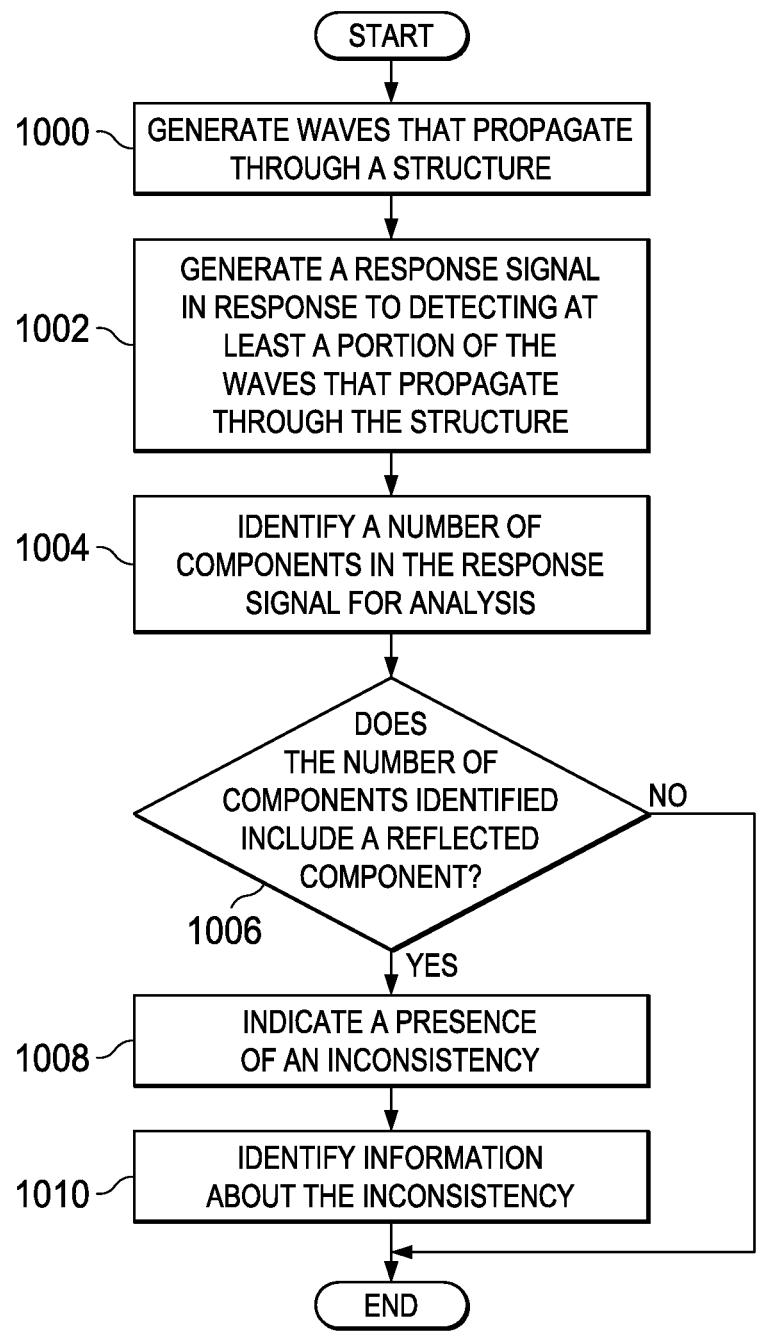
FIG. 10 is an illustration of a flowchart of a process for identifying inconsistencies in accordance with an illustrative embodiment.

With reference now to FIG. 10, an illustration of a flowchart of a process for identifying inconsistencies is depicted in accordance with an illustrative embodiment. The process illustrated in FIG. 10 may be implemented in a detection system, such as detection system 102 in FIG. 1.

The process begins by generating waves that propagate through a structure (operation 1000). The process then generates a response signal in response to detecting at least a portion of the waves that propagate through the structure (operation 1002).

Next, the process identifies a number of components in the response signal for analysis (operation 1004). Operation 1004 may be performed in a number of different ways. For example, operation 1004 may be performed by decomposing the response signal to identify a number of asymmetric components in the response signal. This number of asymmetric components may be the portions of the response signal that correspond to the asymmetric wave modes for the waves that propagated through the structure.

Further, in some illustrative examples, only a selected portion of the response signal may be used to identify the number of components. This selected portion may be the portion of the response signal measured for a selected period of time. This selected period of time may be selected such that the components identified do not correspond to any waves that were reflected off of a boundary or edge of the structure.

A determination is made as to whether the number of components identified include a reflected component (operation 1006). The presence of a reflected component indicates a presence of an inconsistency in the structure. The reflected component may be a component that arrives later than a transmitted component in the number of components and that is more dispersive than the transmitted component.

If the number of components identified includes the reflected component, the process indicates a presence of the inconsistency (operation 1008). This presence may be indicated in a number of different ways. For example, the presence of the inconsistency may be stored in a log, a database, or some other data structure. The indication may be made by sending a message, such as an email message, a text message, or some other signal.

Thereafter, the process then identifies information about the inconsistency (operation 1010), with the process terminating thereafter. With reference again to operation 1006, if the number of components identified does not include a reflected component, the process terminates.

The process illustrated in FIG. 10 may be implemented in detection system 102 in inconsistency detection environment 100 in FIG. 1. This process may be repeated each time a structure is to be examined or interrogated. The process may be repeated periodically or in response to an event. For example, the process may be repeated every 10 seconds, every minute, once a day, or after some other suitable period of time. Further, this process may be initiated in response to an event such as a temperature change, unintended contact with another structure, landing of an aircraft, takeoff of an aircraft, or some other suitable event.

Figure 11:
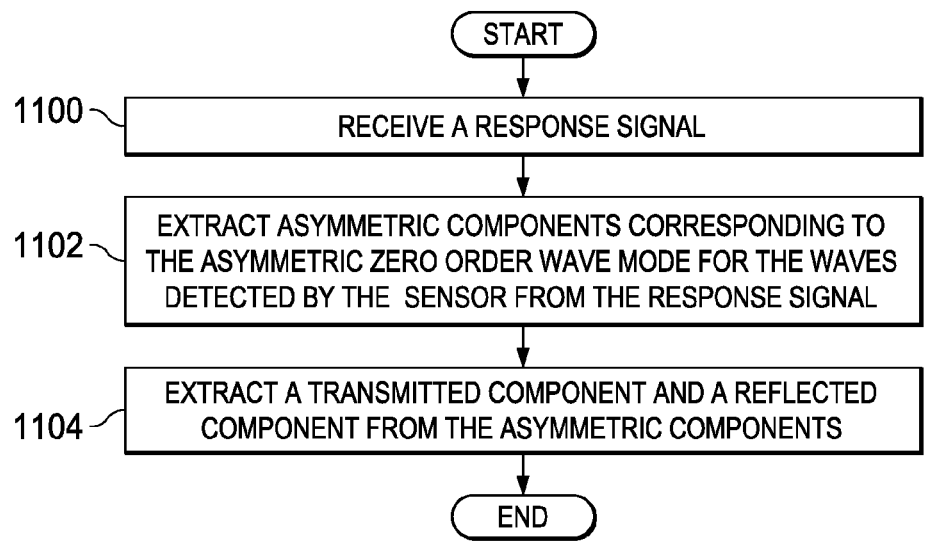
FIG. 11 is an illustration of a flowchart of a process for processing a response signal in accordance with an illustrative embodiment.

With reference now to FIG. 11, an illustration of a flowchart of a process for processing a response signal is depicted in accordance with an illustrative embodiment. The process illustrated in FIG. 11 may be implemented in analyzer 112 in FIG. 1. This process may be used to identify signals for identifying inconsistencies.

The process begins by receiving a response signal (operation 1100). This response signal may have been generated by a transducer functioning as a sensor in response to the transducer detecting waves propagating through a structure. These waves may be Lamb waves that were excited in the structure by a transducer functioning as a transmitter. The transducer functioning as the transmitter may be the same as or different from the transducer functioning as the sensor.

The process extracts asymmetric components corresponding to the asymmetric zero order wave mode for the waves detected by the sensor from the response signal (operation 1102). This process may be implemented using any number of presently available techniques for extracting asymmetric zero order wave modes. These techniques may be referred to as mode decomposition techniques.

Thereafter, the process extracts a transmitted component and a reflected component from the asymmetric components (operation 1104), with the process terminating thereafter. Operation 1104 also may be performed using currently available mode decomposition techniques.

The difference between arrival times for the transmitted component and the reflected component corresponding to the transmitted portion and the reflected portion, respectively, of the waves detected by the transducer functioning as the sensor, may be used to identify and determine whether an inconsistency is present as well as identify information about the inconsistency when one is present.

Figure 12:
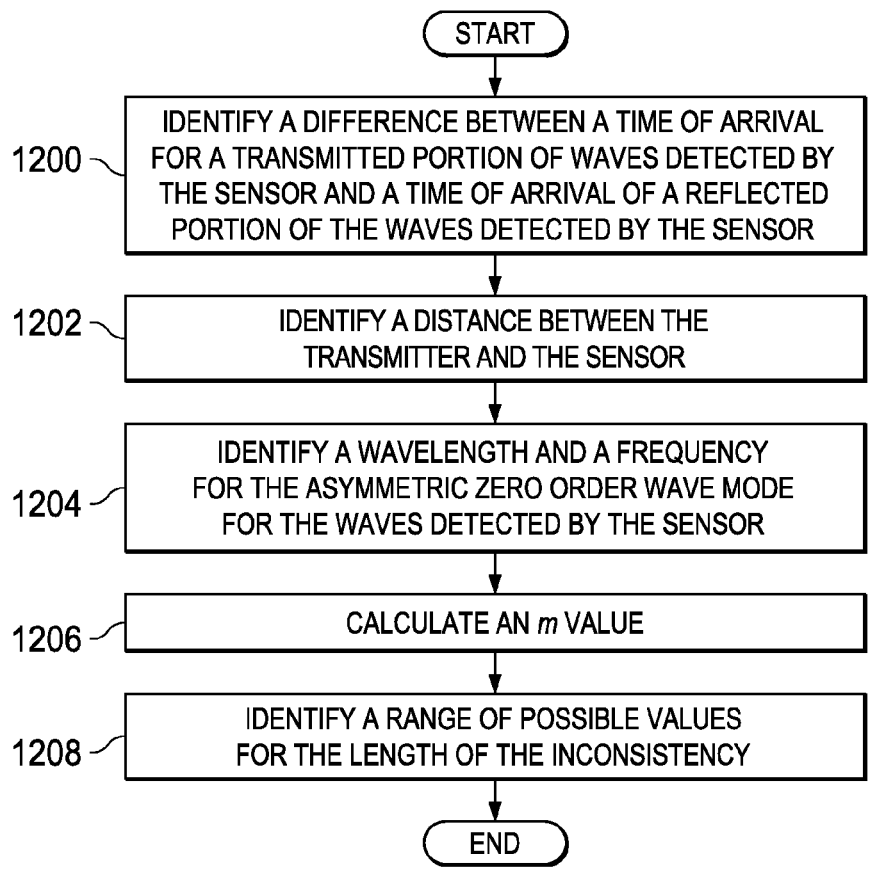
FIG. 12 is an illustration of a flowchart of a process for identifying information about the inconsistency in accordance with an illustrative embodiment.

Turning now to FIG. 12, an illustration of a flowchart of a process for identifying information about the inconsistency is depicted in accordance with an illustrative embodiment. The process illustrated in FIG. 12 may be implemented in detection system 102 in FIG. 1. In particular, this process may be implemented in analyzer 112. The different operations in this flowchart are an example of one manner in which operation 1010 in FIG. 10 may be implemented.

The process begins by identifying a difference between a time of arrival for a transmitted portion of waves detected by the sensor and a time of arrival of a reflected portion of the waves detected by the sensor (operation 1200). The process then identifies a distance between the transmitter and the sensor (operation 1202). The process then identifies a wavelength and a frequency for the asymmetric zero order wave mode for the waves detected by the sensor (operation 1204).

Thereafter, the process calculates an m value (operation 1206). The m value is calculated using the time difference, the wavelength, and the frequency.

The process identifies a range of possible values for the length of the inconsistency (operation 1208), with the process terminating thereafter. The length in operation 1208 may be identified using the m value and the wavelength.

This length may be used to identify a size of the inconsistency. In this example, the size of the inconsistency is identified in a single dimension. This process may be repeated using information from different transducers in the transducer system to identify a shape and size for the inconsistency along a plane.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently or the blocks may sometimes be performed in the reverse order, depending upon the functionality involved. Also, other blocks may be added in addition to the illustrated blocks in a flowchart or block diagram.

Figure 13:
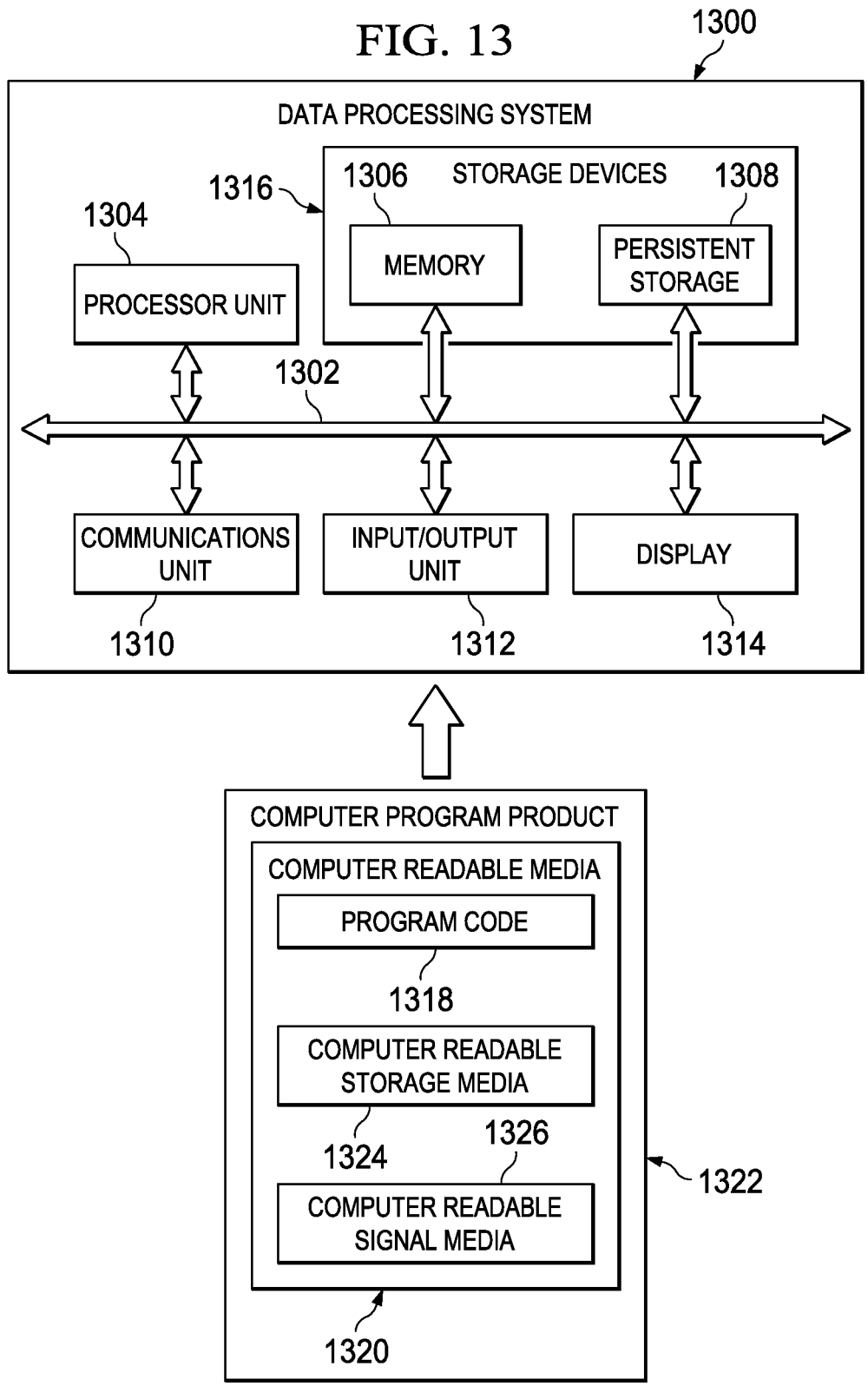
FIG. 13 is an illustration of a data processing system in accordance with an illustrative embodiment.

Turning now to FIG. 13, an illustration of a data processing system is depicted in accordance with an illustrative embodiment. Data processing system 1300 may be used to implement one or more computers in computer system 115 in FIG. 1. In particular, data processing system 1300 is an illustration of one manner in which hardware for analyzer 112 may be implemented. In this illustrative example, data processing system 1300 includes communications framework 1302, which provides communications between processor unit 1304, memory 1306, persistent storage 1308, communications unit 1310, input/output (I/O) unit 1312, and display 1314. In this example, communications framework 1302 may take the form of a bus system.

Processor unit 1304 serves to execute instructions for software that may be loaded into memory 1306. Processor unit 1304 may be a number of processors, a multi-processor core, or some other type of processor, depending on the particular implementation.

Memory 1306 and persistent storage 1308 are examples of storage devices 1316. A storage device is any piece of hardware that is capable of storing information such as, for example, without limitation, data, program code in functional form, and other suitable information either on a temporary basis or a permanent basis. Storage devices 1316 may also be referred to as computer readable storage devices in these illustrative examples. Memory 1306, in these examples, may be, for example, a random access memory or any other suitable volatile or non-volatile storage device. Persistent storage 1308 may take various forms, depending on the particular implementation.

For example, persistent storage 1308 may contain one or more components or devices. For example, persistent storage 1308 may be a hard drive, a flash memory, a rewritable optical disk, a rewritable magnetic tape, or some combination of the above. The media used by persistent storage 1308 also may be removable. For example, a removable hard drive may be used for persistent storage 1308.

Communications unit 1310, in these illustrative examples, provides for communications with other data processing systems or devices. In these illustrative examples, communications unit 1310 is a network interface card.

Input/output unit 1312 allows for input and output of data with other devices that may be connected to data processing system 1300. For example, input/output unit 1312 may provide a connection for user input through a keyboard, a mouse, and/or some other suitable input device. Further, input/output unit 1312 may send output to a printer. Display 1314 provides a mechanism to display information to a user.

Instructions for the operating system, applications, and/or programs may be located in storage devices 1316, which are in communication with processor unit 1304 through communications framework 1302. The processes of the different embodiments may be performed by processor unit 1304 using computer-implemented instructions, which may be located in a memory, such as memory 1306.

These instructions are referred to as program code, computer usable program code, or computer readable program code that may be read and executed by a processor in processor unit 1304. The program code in the different embodiments may be embodied on different physical or computer readable storage media, such as memory 1306 or persistent storage 1308.

Program code 1318 is located in a functional form on computer readable media 1320 that is selectively removable and may be loaded onto or transferred to data processing system 1300 for execution by processor unit 1304. Program code 1318 and computer readable media 1320 form computer program product 1322 in these illustrative examples. In one example, computer readable media 1320 may be computer readable storage media 1324 or computer readable signal media 1326.

In these illustrative examples, computer readable storage media 1324 is a physical or tangible storage device used to store program code 1318 rather than a medium that propagates or transmits program code 1318.

Alternatively, program code 1318 may be transferred to data processing system 1300 using computer readable signal media 1326. Computer readable signal media 1326 may be, for example, a propagated data signal containing program code 1318. For example, computer readable signal media 1326 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1300 are not meant to provide architectural limitations to the manner in which different embodiments may be implemented. The different illustrative embodiments may be implemented in a data processing system including components in addition to and/or in place of those illustrated for data processing system 1300. Other components shown in FIG. 13 can be varied from the illustrative examples shown. The different embodiments may be implemented using any hardware device or system capable of running program code 1318.

Illustrative embodiments of the disclosure may be described in the context of aircraft manufacturing and service method 1400 as shown in FIG. 14 and aircraft 1500 as shown in FIG. 15. Turning first to FIG. 14, an illustration of an aircraft manufacturing and service method is depicted in accordance with an illustrative embodiment. During pre-production, aircraft manufacturing and service method 1400 may include specification and design 1402 of aircraft 1500 in FIG. 15 and material procurement 1404.

During production, component and subassembly manufacturing 1406 and system integration 1408 of aircraft 1500 in FIG. 15 takes place. Thereafter, aircraft 1500 in FIG. 15 may go through certification and delivery 1410 in order to be placed in service 1412. While in service 1412 by a customer, aircraft 1500 in FIG. 15 is scheduled for routine maintenance and service 1414, which may include modification, reconfiguration, refurbishment, and other maintenance or service.

Each of the processes of aircraft manufacturing and service method 1400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 15, an illustration of an aircraft is depicted in which an illustrative embodiment may be implemented. In this example, aircraft 1500 is produced by aircraft manufacturing and service method 1400 in FIG. 14 and may include airframe 1502 with plurality of systems 1504 and interior 1506. Examples of systems 1504 include one or more of propulsion system 1508, electrical system 1510, hydraulic system 1512, and environmental system 1514. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1400 in FIG. 14.

In one illustrative example, components, subassemblies, and other structures produced during components and subassembly manufacturing 1406 may be tested using inspection system 152. Additionally, one or more illustrative embodiments may be implemented and used while aircraft 1500 is in service 1412. For example, inspection system 152 may operate during flight of aircraft 1500 to inspect structures in aircraft 1500. As another illustrative example, inspection system 152 may be implemented or added to aircraft 1500 during system integration 1408 or maintenance and service 1414.

Thus, one or more illustrative embodiments provide a method and apparatus for identifying inconsistencies. In one illustrative embodiment, a method is provided for identifying an inconsistency. A number of waves that propagate through a structure are generated. A response signal is generated in response to detecting at least a portion of the number of waves that propagate through the structure. A determination is made as to whether the response signal includes a reflected component. A presence of an inconsistency in the structure is indicated when the response signal includes the reflected component.

As a result, changes in the structure or changes in the use of the structure can occur without increasing false positives as compared to detection systems that use a baseline of signals for comparison. For example, temperature variations and changes in loading of a structure may not affect the identification of inconsistencies using an illustrative embodiment. In this manner, false indications occurring from unrelated conditions that do not result in inconsistencies may be reduced.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying an inconsistency, the method comprising:
    generating a number of waves that propagate through a structure;
    generating a response signal in response to detecting at least a portion of the number of waves that propagate through the structure;
    determining whether the response signal includes a reflected component;
    indicating a presence of the inconsistency in the structure when the response signal includes the reflected component; and
    identifying information about the inconsistency by identifying an m value, wherein the m value is half of a product of a central frequency for the number of waves and a difference in arrival time of a transmitted portion and a reflected portion of the at least a portion of the number of waves detected.

2. The method of claim 1, wherein the at least a portion of the number of waves is detected in one of a pitch-catch mode and a pulse-echo mode.

3. The method of claim 1, wherein determining whether the response signal includes the reflected component comprises:
    identifying a number of components in the response signal; and
    determining whether the number of components in the response signal includes the reflected component.

4. The method of claim 1 further comprising:
    identifying information about the inconsistency using the difference in arrival time of the transmitted portion and the reflected portion of the at least a portion of the number of waves detected.

5. The method of claim 4, wherein the information includes at least one of a size of the inconsistency, an indice for the inconsistency, and a range of possible values for a length of the inconsistency.

6. The method of claim 4, wherein the waves are generated using a first transducer positioned relative to the structure and the response signal is generated using a second transducer positioned relative to the structure in which the inconsistency is located between the first transducer and the second transducer and wherein identifying the information about the inconsistency comprises:
    identifying an upper limit for a range of possible values for a length of the inconsistency using a first time when the transmitted portion was detected and a second time when the reflected portion was detected and a distance between the first transducer and the second transducer.

7. The method of claim 4, wherein identifying the information about the inconsistency further comprises:
    identifying a range of possible values for a length of the inconsistency using the m value, a first velocity for the reflected portion through the inconsistency, the central frequency, and an assumption that the first velocity for the reflected portion is lower than a second velocity for the transmitted portion through an area in the structure in which the inconsistency is not present.

8. The method of claim 1, wherein the m value indicates a level of severity of the inconsistency with respect to stiffness.

9. The method of claim 1, wherein generating the number of waves that propagate through the structure comprises:
    generating a number of Lamb waves that propagate through the structure using a transducer configured to function as a transmitter.

10. The method of claim 9, wherein generating the number of Lamb waves comprises:
    exciting an asymmetric zero order wave mode for the number of Lamb waves that propagate through the structure using the transducer configured to function as the transmitter.

11. The method of claim 1, wherein the structure is for a platform, and the platform is an aircraft.

12. An apparatus comprising:
    a transducer system configured to be associated with a structure and configured to generate a number of waves that propagate through the structure and generate a response signal in response to detecting at least a portion of the number of waves that propagate through the structure; and
    an analyzer configured to:
        control the transducer system to receive the response signal from the transducer system;
        determine whether the response signal includes a reflected component;
        indicate a presence of an inconsistency in the structure when the response signal includes the reflected component; and
        identify information about the inconsistency by identifying an m value, wherein the m value is half of a product of a central frequency for the number of waves and a difference in arrival time of a transmitted portion and a reflected portion of the at least a portion of the number of waves detected.

13. The apparatus of claim 12, wherein the transducer system is further configured to detect the at least a portion of the number of waves in one of a pitch-catch mode and a pulse-echo mode.

14. The apparatus of claim 12, wherein in being configured to determine whether the response signal includes the reflected component, the analyzer is configured to identify a number of components in the response signal; and determine whether the number of components in the response signal includes the reflected component.

15. The apparatus of claim 12, wherein the analyzer is further configured to identify information about the inconsistency using the difference in arrival time of the transmitted portion and the reflected portion of the at least a portion of the number of waves detected in which the information includes at least one of a size of the inconsistency, an indice for the inconsistency, and a range of possible values for a length of the inconsistency.

16. The apparatus of claim 12, wherein the transducer system comprises:
a first transducer configured to be positioned relative to the structure and configured to generate the number of waves; and
a second transducer configured to be positioned relative to the structure and configured to generate the response signal, wherein the inconsistency is located between the first transducer and the second transducer.

17. The apparatus of claim 15, wherein in being configured to identify the information about the inconsistency, the analyzer is configured to identify the range of possible values for the length of the inconsistency using the m value, a first velocity for the reflected portion through the inconsistency, the central frequency, and an assumption that the first velocity for the reflected portion is lower than a second velocity for the transmitted portion through an area in the structure in which the inconsistency is not present.

18. The apparatus of claim 12, wherein the m value indicates a level of severity of the inconsistency with respect to stiffness.

19. The apparatus of claim 12, wherein the number of waves takes a form of a number of Lamb waves and wherein the transducer system is configured to excite an asymmetric zero order wave mode for the number of Lamb waves to generate the number of Lamb waves that propagate through the structure.

* * * * *